(12) United States Patent
Shankar (10) Patent No.: US 8,185,182 B1
(45) Date of Patent: May 22, 2012

(54) NONINVASIVE GLUCOSE MEASUREMENT (76) Inventor: Ravi Shankar, Boca Raton, FL (US)

( * ) Notice: Subject to any disclaimer, the term of this patent is extended or adjusted under 35 U.S.C. 154(b) by 535 days.

(21) Appl. No.: 12/381,242

(22) Filed: Mar. 10, 2009

Related U.S. Application Data (60) Provisional application No. 61/196,160, filed on Oct. 14, 2008, provisional application No. 61/068,060, filed on Mar. 10, 2008.

(51) Int. Cl.
*A61B 5/05* (2006.01)
*A61B 5/00* (2006.01)

(52) U.S. Cl. ............... 600/347; 600/345; 600/365

(58) Field of Classification Search .......... 600/345–371, 600/547, 309–323
See application file for complete search history.

(56) References Cited

U.S. PATENT DOCUMENTS

| | | | | |
|---|---|---|---|---|
| 4,144,878 A | * | 3/1979 | Wheeler | 600/506 |
| 4,204,545 A | * | 5/1980 | Yamakoshi | 600/506 |
| 4,432,374 A | * | 2/1984 | Osanai | 600/507 |
| 4,875,488 A | * | 10/1989 | Shimazu et al. | 600/507 |
| 5,137,023 A | * | 8/1992 | Mendelson et al. | 600/316 |
| 5,241,963 A | * | 9/1993 | Shankar | 600/481 |
| 5,297,556 A | * | 3/1994 | Shankar | 600/481 |
| 5,313,941 A | * | 5/1994 | Braig et al. | 600/322 |
| 5,343,867 A | * | 9/1994 | Shankar | 600/481 |
| 5,630,424 A | * | 5/1997 | Raines et al. | 600/507 |
| 5,718,232 A | * | 2/1998 | Raines et al. | 600/507 |
| 6,128,518 A | * | 10/2000 | Billings et al. | 600/345 |
| 6,152,881 A | * | 11/2000 | Raines et al. | 600/507 |
| 6,766,191 B1 | * | 7/2004 | Billings et al. | 600/547 |
| 6,961,598 B2 | * | 11/2005 | Diab | 600/310 |
| 2002/0155615 A1 | * | 10/2002 | Novikov et al. | 436/149 |
| 2003/0220581 A1 | * | 11/2003 | Ollmar et al. | 600/547 |
| 2006/0029991 A1 | * | 2/2006 | Hagino et al. | 435/14 |
| 2007/0060803 A1 | * | 3/2007 | Liljeryd et al. | 600/301 |

OTHER PUBLICATIONS

Yamakoshi, Ken-Ichi; Shimazu, Hideaki; Togawa, Tatsuo; Fukuoka, Masakazu; Ito, Hiroshi; , "Noninvasive Measurement of Hematocrit by Electrical Admittance Plethysmography Technique," Biomedical Engineering, IEEE Transactions on , vol. BME-27, No. 3, pp. 156-161, Mar. 1980. doi: 10.1109/TBME.1980.326617.*

Raine NM, Sneddon JC. A simple water-filled plethysmograph for measurement of limb blood flow in humans. Adv Physiol Educ. Jun. 2002; vol. 26: No. 2.*

Shankar, et al. "The Contribution of Vessel Volume and Blood Resistivity Change to Electrical Impedance Pulse" IEEE Tran. Biomed. Eng. vol. BME-32, No. 3, pp. 192-198, Mar. 1985.

* cited by examiner

*Primary Examiner* — Navin Natnithithadha
*Assistant Examiner* — Sunita Reddy
(74) *Attorney, Agent, or Firm* — Alvin S. Blum (57) ABSTRACT

An apparatus and method for measuring the blood glucose level of a diabetic using insulin is noninvasive. The apparatus includes two plethysmographs that sense the blood in two fingers simultaneously. The electrodes in the plethysmographs are immersed in conductive liquids. One liquid has electric conductivity equal to blood. The other liquid is more conductive than blood. Signals from the fingers are compared to signals obtained earlier when glucose levels were known from conventional measurements. An alternative embodiment employs a single plethysmograph with one set of electrodes in a surrounding chamber and a second set of electrodes against the skin surface.

6 Claims, 12 Drawing Sheets

NONINVASIVE GLUCOSE MEASUREMENT

This application claims the benefit of provisional applications for patent Ser. Nos. 61/068,060 filed Mar. 10, 2008, and 61/196,160 filed Oct. 14, 2008.

FIELD OF THE INVENTION

This invention relates generally to apparatus and method for monitoring the blood level of glucose in people, and more particularly to such apparatus and method that do not involve invading the body to determine the blood glucose level.

BACKGROUND OF THE INVENTION

It has been shown that avoiding high glucose levels and low glucose levels by the correct timing and control of food intake and insulin injection enhances both short term and long term health in type 1 diabetics. It is important to closely monitor the blood glucose level in type 1 diabetics in order to better control glucose levels. Conventional monitoring of blood glucose levels is usually done by extracting blood samples and measuring the level in the sample by convenient and readily available instruments. Patients are reluctant to take the samples as often as they should. It would be useful to have a noninvasive blood glucose measuring device to improve patient compliance.

SUMMARY OF THE INVENTION

It is accordingly an object of the invention to provide a noninvasive blood glucose monitoring device that would enable the patient to know when the blood glucose level is out of the normal range so that proper measures could promptly be taken to correct the problem. The apparatus and method of the invention provides two plethysmography devices to each encircle a finger of the subject. One device has the signal electrodes in a liquid having the same electrical conductivity as the finger blood. The other device has the electrodes in a liquid having electrical conductivity much greater than the finger blood. The apparatus is calibrated by obtaining signals when blood glucose level is known. Processing the signals and comparing them with the calibration values by a data processor provides determination of the blood glucose level at the time without drawing a sample.

These and other objects, features, and advantages of the invention will become more apparent from the detailed description of an exemplary embodiment thereof as illustrated in the accompanying drawings, in which like elements are designated by like reference characters in the various drawing figures.

DETAILED DESCRIPTION OF PREFERRED EMBODIMENTS

Figure 1:
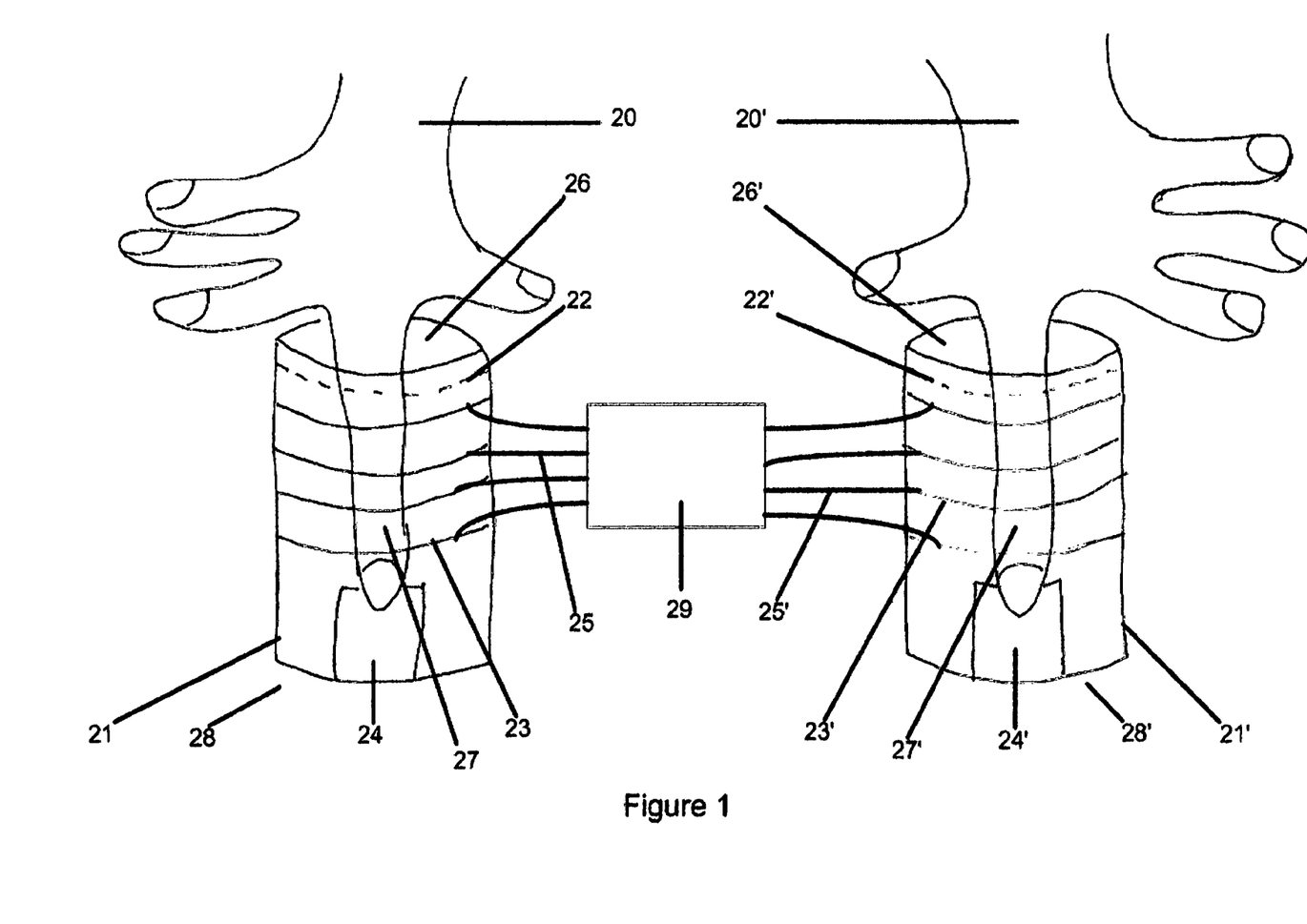
FIG. 1 is a perspective view of the first embodiment.
Figure 2:
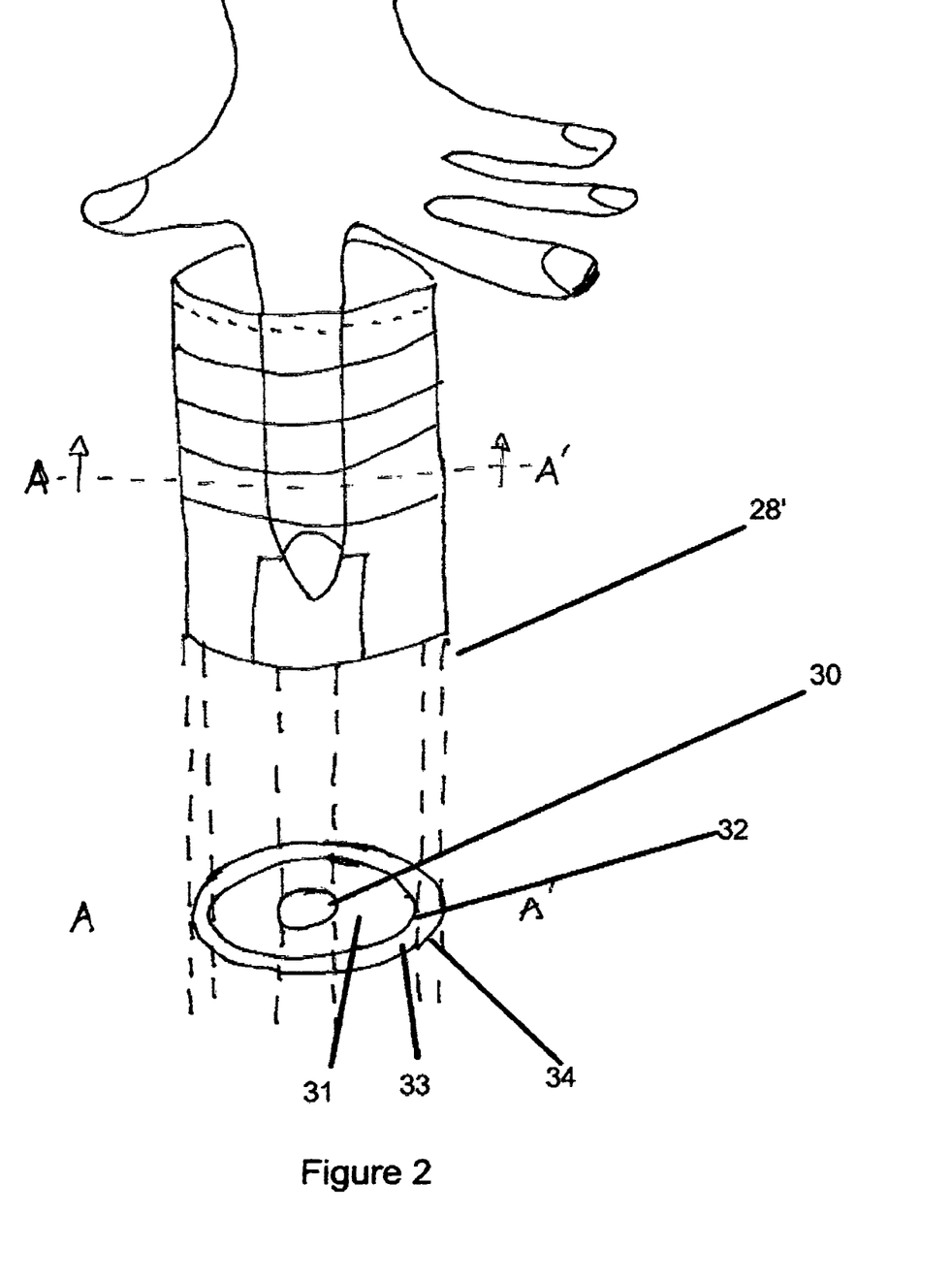
FIG. 2 is a cross-sectional view of the first embodiment.
Figure 3:
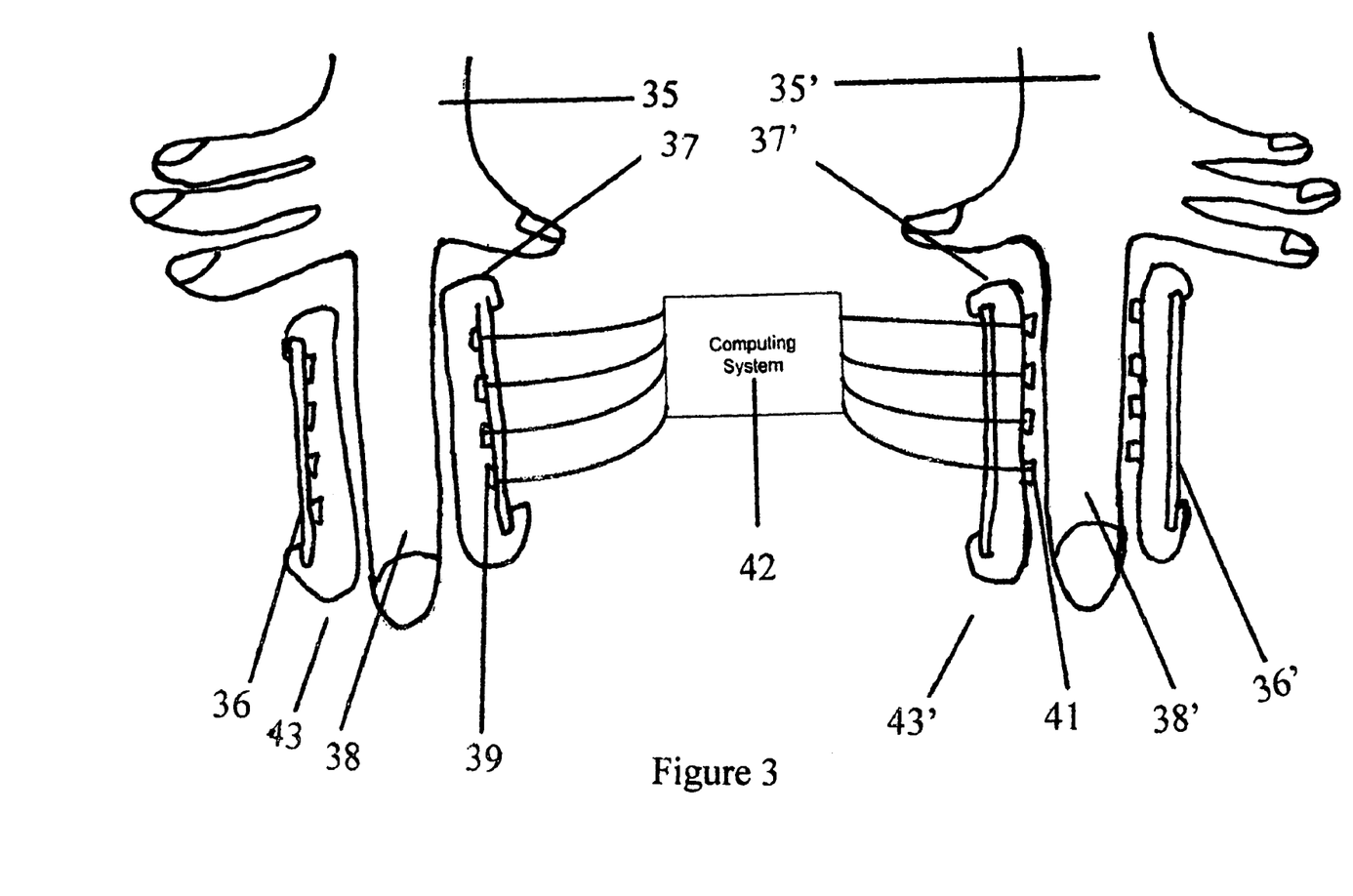
FIG. 3 is a perspective view of the second embodiment.
Figure 4:
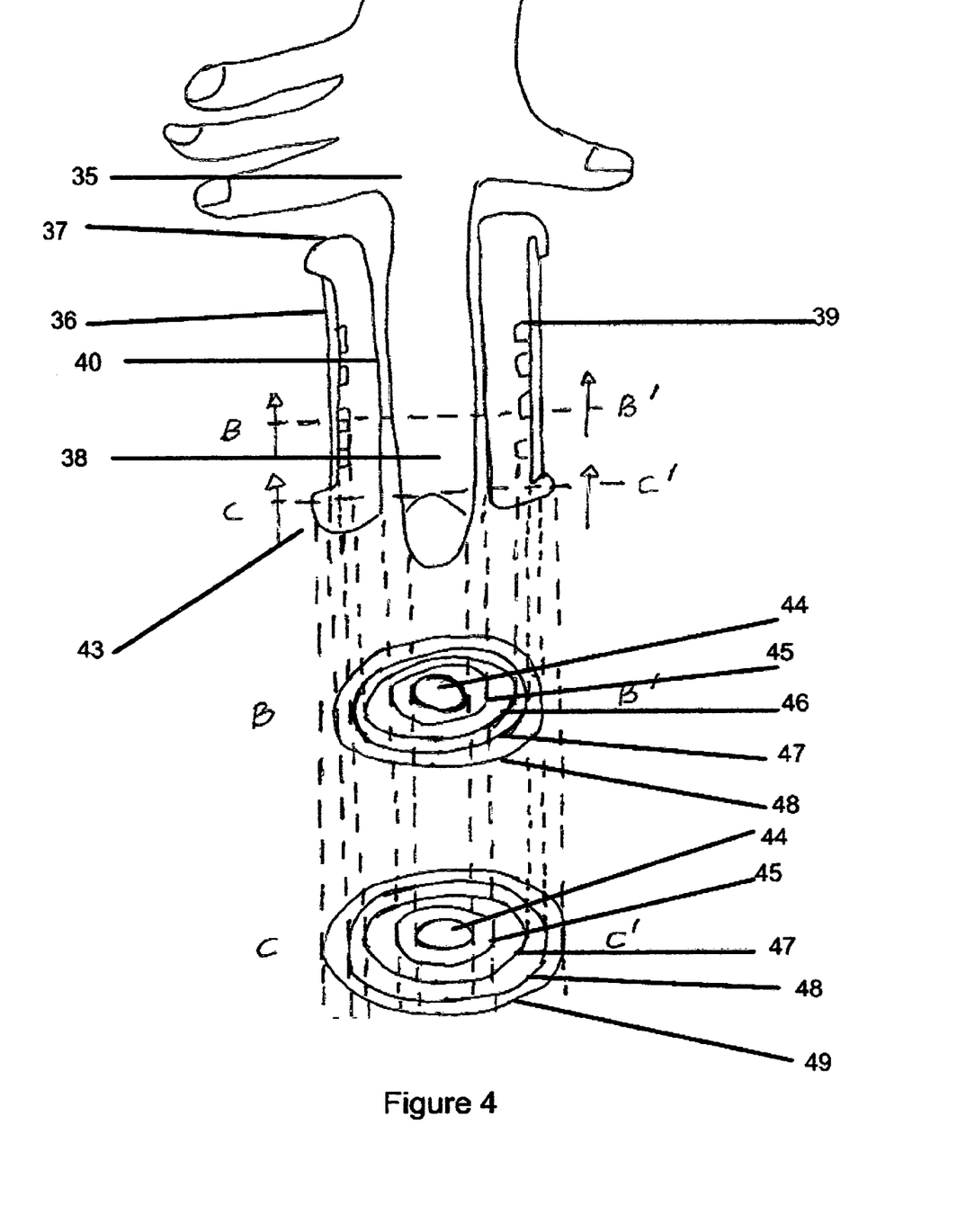
FIG. 4 is a cross-sectional view of the second embodiment.
Figure 5:
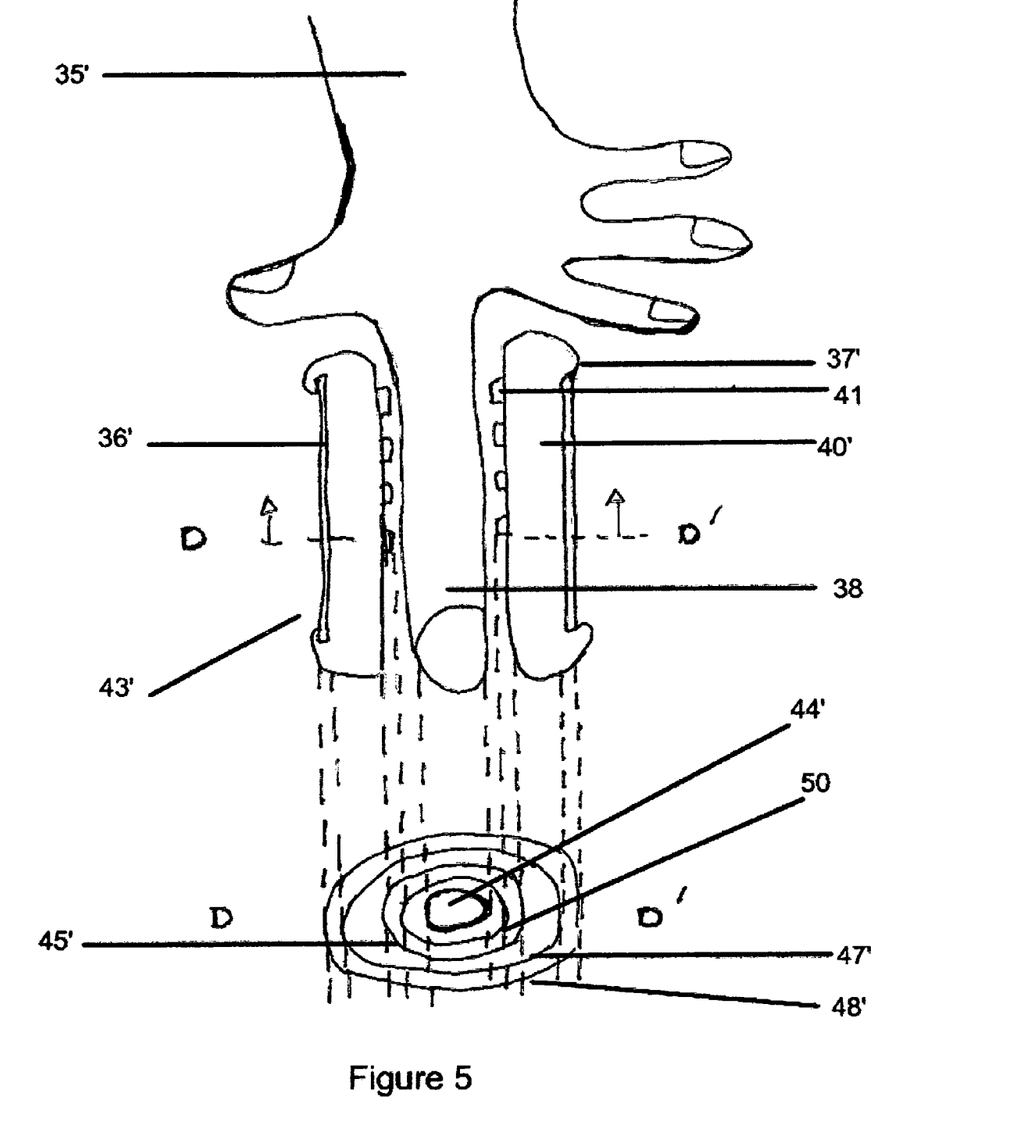
FIG. 5 is another cross-sectional view of the second embodiment.
Figure 6:
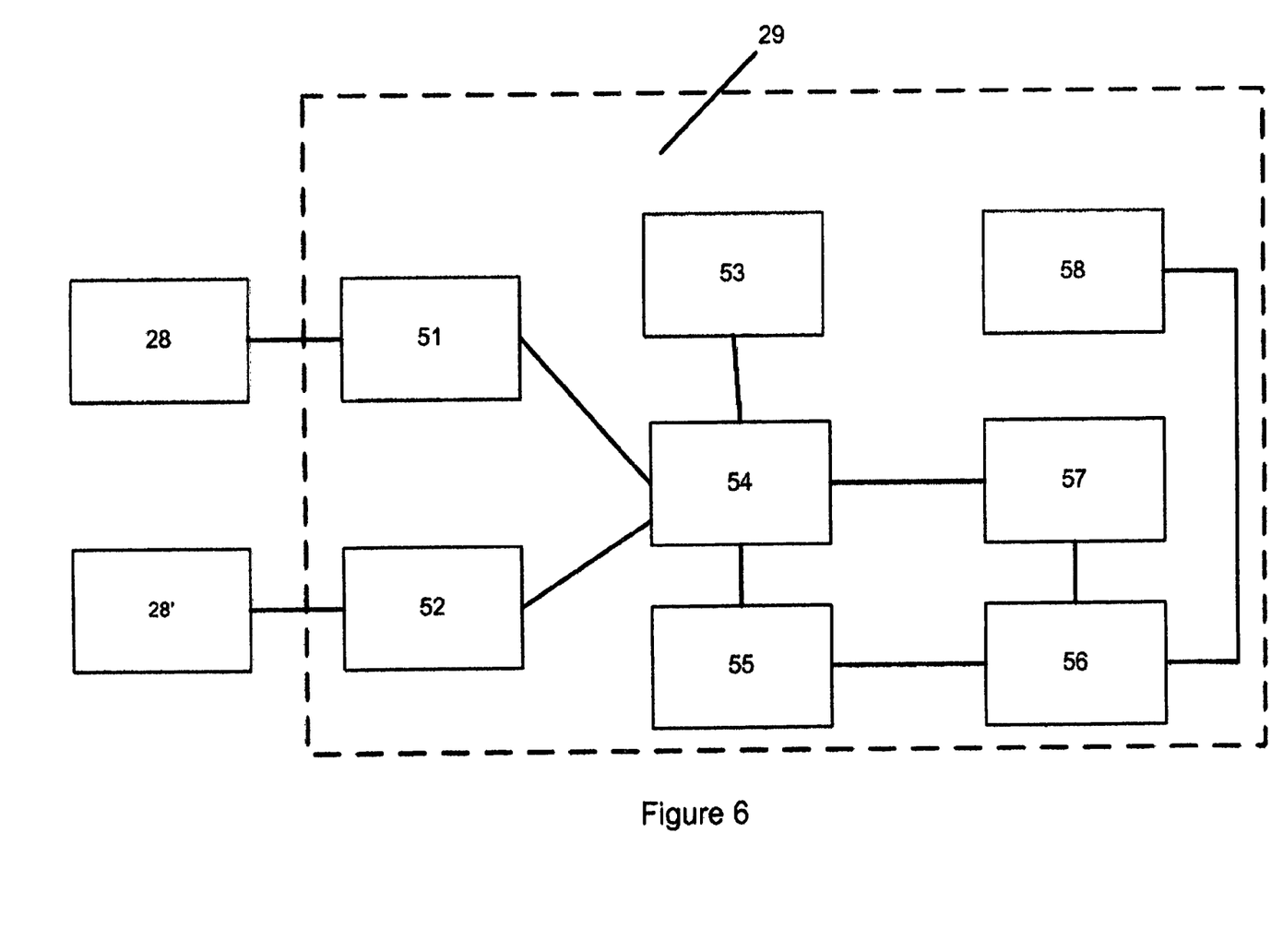
FIG. 6 is the block diagram of the computing system for the first embodiment.

I describe the principle behind the system with the aid of the drawing FIGS. 1 and 2. They describe the first embodiment. FIGS. 3 and 4 apply the same principle, but implement in a second way, thus representing the second embodiment. FIGS. 5 and 6 also apply the same principle, but implement in a third way, thus representing the third embodiment.

It is well known that an impedance plethysmograph can be used to obtain resistance pulse signal of a limb segment as the blood pressure pulse propagates through it. An impedance plethysmograph typically uses 4 electrodes. The two outer electrodes are called current electrodes and are used to apply a constant high frequency current. The two inner electrodes are called signal electrodes and are used to acquire a pulsatile voltage signal that can be divided by the applied constant current magnitude to yield the resistance pulse signal. This resistance pulse signal has two components, due to vessel wall movement and due to blood cell movement, both in the major artery of that limb segment. The first one causes a change in cross-section of the artery, while the second one causes a change in blood resistivity of the blood in the artery. It is well known that Resistance of an electrically conductive medium is directly proportion to the resistivity of the conducting medium (blood, in our case) and inversely proportional to the area of cross section (arterial cross section, in our case). This invention separates these two signals using the embodiments described below, and uses their respective changes with respect to their averages, to identify blood glucose level that is high or low relative to the patient's normal blood glucose level. The impetus for this derives from the fact that the resistance pulse signal masks individual variations of these two pulse signal components, leading to varying sensitivity and specificity even in the same person. It is customary to call the pulse signal due to cross-sectional area change as the volume pulse or the artery volume pulse. The same will be used in this description. The pulse signal due to blood resistivity change is herein identified as the resistivity pulse.

For embodiment 1, refer to FIGS. 1 and 2.

In FIG. 1, refer to the assembly identified as 28. The right index finger 27 (digit R) of right hand 20 is shown immersed in a plastic beaker 21 (the first chamber) partially filled to level 22 with salt water. Four aluminum electrodes 23 (first electrode assembly) are glued to the inside of the plastic beaker 21. These are connected through the electrode leads 25 to a computing system 29. The outer aluminum electrodes of 23 are the current electrodes, while the inner electrodes are the spaced-apart signal electrodes. Support for the finger tip 24 and the snug fitting foam 26 ensure that the finger is held stationary, so motion artifacts are reduced. This improves signal reproducibility. The salt water is adjusted to have electrical conductivity close to the flowing blood. A salt concentration of about 9 g per liter of water achieves this. Continuing with embodiment 1, refer to the assembly identified as 28' in FIG. 1. The left index finger 27' (digit L) of left hand 20' is shown immersed in a plastic beaker 21' (the second chamber) partially filled to level 22' with salt water. Four aluminum electrodes 23' (first electrode assembly) are glued to the inside of the plastic beaker 21'. These are connected through the electrode leads 25' to a computing system 29. The outer aluminum electrodes of 23' are the current electrodes, while the inner electrodes are the spaced-apart signal electrodes. Support for the finger tip 24' and the snug fitting foam 26' ensure that the finger is held stationary, so motion artifacts are reduced. This improves signal reproducibility. The salt water is adjusted to have higher electrical conductivity relative to the flowing blood. A salt concentration substantially higher than 9 g per liter of water achieves this.

Use of a rigid chamber ensures that an equal amount of salt water is displaced when the artery expands. Thus, if the salt conductivity is close to that of the flowing blood, the artery volume pulse due to artery expansion will be canceled out by an equal and opposite saline volume pulse. The remaining component, the net signal recorded between the spaced-apart signal electrodes, will be dominated by the resistivity pulse. This is the output of the right hand side assembly 28' and is designated here as PR. If the salt conductivity is substantially higher than that of flowing blood (say by a factor of 2 or 3), then the net signal will be dominated by the saline volume pulse which is a magnified (inverse) version of the blood volume pulse. This is the output of the left hand side assembly 28 and is designated here as PL.

These signals are acquired as amplitude modulating signals and are demodulated inside the computing system, where they are subject to signal processing, and then used in estimating the blood glucose level. An initial step of instrument calibration with known glucose levels is also conducted. All this will be explained in a common section below, after a brief discussion of the second embodiment. FIG. 2 depicts the cross-sectional view of the first embodiment, as obtained at the section AA'. I show for the right hand assembly 28'. The cross-sectional view of the left hand assembly 28 would be exactly identical. In the cross-sectional view, 30 is the cross section of the digit, 31 is the region occupied by the salt water (saline), and 32 is the aluminum electrode, which is glued with glue 33 to the inner surface 34 of the rigid chamber.

For embodiment 2, refer to FIGS. 3, 4, and 5. In FIG. 3, refer to the assembly identified as 43. The left index finger 38 (digit R) of left hand 35 is shown surrounded by a unit that is used to measure the volume pulse. It is a digit encircling liquid chamber that has a thin flaccid rubber membrane 37 (the flexible inner wall) next to the skin of the digit 38 and is folded over and cemented to a rigid exterior plastic sheet 36 (the rigid outer wall). The rubber membrane folds over the rigid exterior sheet at both top and bottom, thus leading to a sealed unit. Salt water is inserted into this sealed unit via a hole made with a syringe at the top of the flaccid membrane 37. The hole is then sealed after the liquid chamber is partially filled. The annular volume of this liquid chamber is defined by the encircling rigid outer wall 36. A first electrode assembly 39 is affixed to the inner surface of the outer wall. This assembly includes a first pair of spaced-apart signal electrodes and a pair of current electrodes above and below the signal electrodes. A current is fed into the chamber through these outer electrodes. The salt water is adjusted to have electrical conductivity close to the flowing blood. A salt concentration of about 9 g per liter of water achieves this.

Continuing with embodiment 2, refer to the assembly identified as 43' in FIG. 3. The right index finger 38' (digit L) of right hand 35' is shown surrounded by a unit that is used to measure the resistance pulse. It is a digit encircling liquid chamber that has a thin flaccid rubber membrane 37' (the flexible inner wall) next to the skin of the digit 38' and is folded over and cemented to a rigid exterior plastic sheet 36' (the rigid outer wall). The rubber membrane folds over the rigid exterior sheet at both top and bottom, thus leading to a sealed unit. Salt water is inserted into this sealed unit via a hole made with a syringe at the top of the flaccid membrane 37'. The hole is then sealed after the liquid chamber is partially filled. The annular volume of this liquid chamber is defined by the encircling rigid outer wall 36'. A second electrode assembly 41 is affixed to the surface of the inner wall that contacts the digit. This assembly includes a second pair of spaced-apart signal electrodes and a pair of current electrodes over and below the signal electrodes. A current is fed into the chamber through these outer electrodes. The salt water is adjusted to have electrical conductivity close to the flowing blood. A salt concentration of about 9 g per liter of water achieves this. Unlike the first embodiment, the flaccid inner wall serves to electrically separate the salt chamber from the digit. Use of a rigid chamber, however, still ensures that an equal amount of salt water is displaced when the artery expands. Thus, with a salt conductivity close to that of the flowing blood, the saline volume pulse will be equal and opposite to the volume pulse that occurs due to artery expansion. Thus, the resistance pulse recorded from the left hand side assembly 43 will be predominantly a measure of the volume pulse. On the other hand, the resistance pulse recorded from the right hand assembly 43' directly records the resistance pulse from the digit and thus has both the volume pulse and resistivity pulse contributions. Thus, one can obtain the resistivity pulse by adding the resistance pulse signal from the left hand side unit 43 to the resistance pulse obtained from the right hand side unit 43'. This computation is easily achieved within the Computing system 42.

The output of the right hand side assembly 43' is designated here as PR'. The signal obtained with the left hand side assembly 43 is a saline volume pulse which is approximately equal (but inverted) to the blood volume pulse. This is the output of the left hand side assembly 43 and is designated here as PL'.

These signals are acquired as amplitude modulating signals and are demodulated inside the computing system, where they are subject to signal processing, and then used in estimating the blood glucose level. An initial step of instrument calibration with known glucose levels is also conducted. All this will be explained in a common section below, after a brief discussion of the third embodiment.

FIG. 4 depicts two cross-sectional views of the second embodiment, at sections BB' and CC'. I show this for the left hand assembly 43. The CC' cross-sectional view of the right hand assembly 43' is exactly identical. However, the cross-sectional view of the right hand assembly 43' differs with regard to the electrode positions, as shown with FIG. 5 and the cross-section DD' for the right hand side assembly 43'. In the cross-sectional view, BB' of FIG. 4, 44 is the cross section of the digit, 45 is the flaccid thin inner wall of the encircling chamber, 46 is the aluminum electrode that is glued to the inner surface of the outer rigid wall, represented by 47. The rigid outer wall comprises of the outer cross-sections 47 and 48. The region between 45 and 47 is the region occupied by the salt water (saline or other salt providing the electrical conductivity). In the cross-sectional view CC' of FIG. 4, 44 is the cross section of the digit, and 45 is the flaccid thin inner wall of the encircling chamber. The rigid outer wall is comprised of 47 and 48. The outermost outline 49 corresponds to the folded over section of the thin inner membrane 37. This membrane is folded over the rigid outer wall exterior 48 and cemented, at both top and bottom of the assembly. FIG. 5 depicts one cross-sectional view of the second embodiment, at sections DD'. I show this for the right hand assembly 43'. In this cross-sectional view, DD' of FIG. 5, 44' is the cross section of the digit, and 50 is the aluminum electrode glued to the digit side of the thin inner membrane 45'. The rigid outer wall is represented by 47' and 48'.

Embodiment 3 is obtained by gluing the two electrode sets on to the same overall assembly for one digit, 43. This will be in addition to the first electrode assembly of the left hand side that obtains the saline volume pulse, a second electrode assembly is affixed to the outer surface of the inner wall that contacts the digit. This will be similar to the assembly 43'. This combines both of them onto one embodiment so all measurements can be made on one digit. The insulation property of the inner wall should ideally separate the electrical activity on the two sides of the thin membrane. However, it is advised that two different carrier frequencies (Say 100 kHz and 125 kHz) be used for the first and second current sources, to avoid any interference. This is explained more below.

Figure 8:
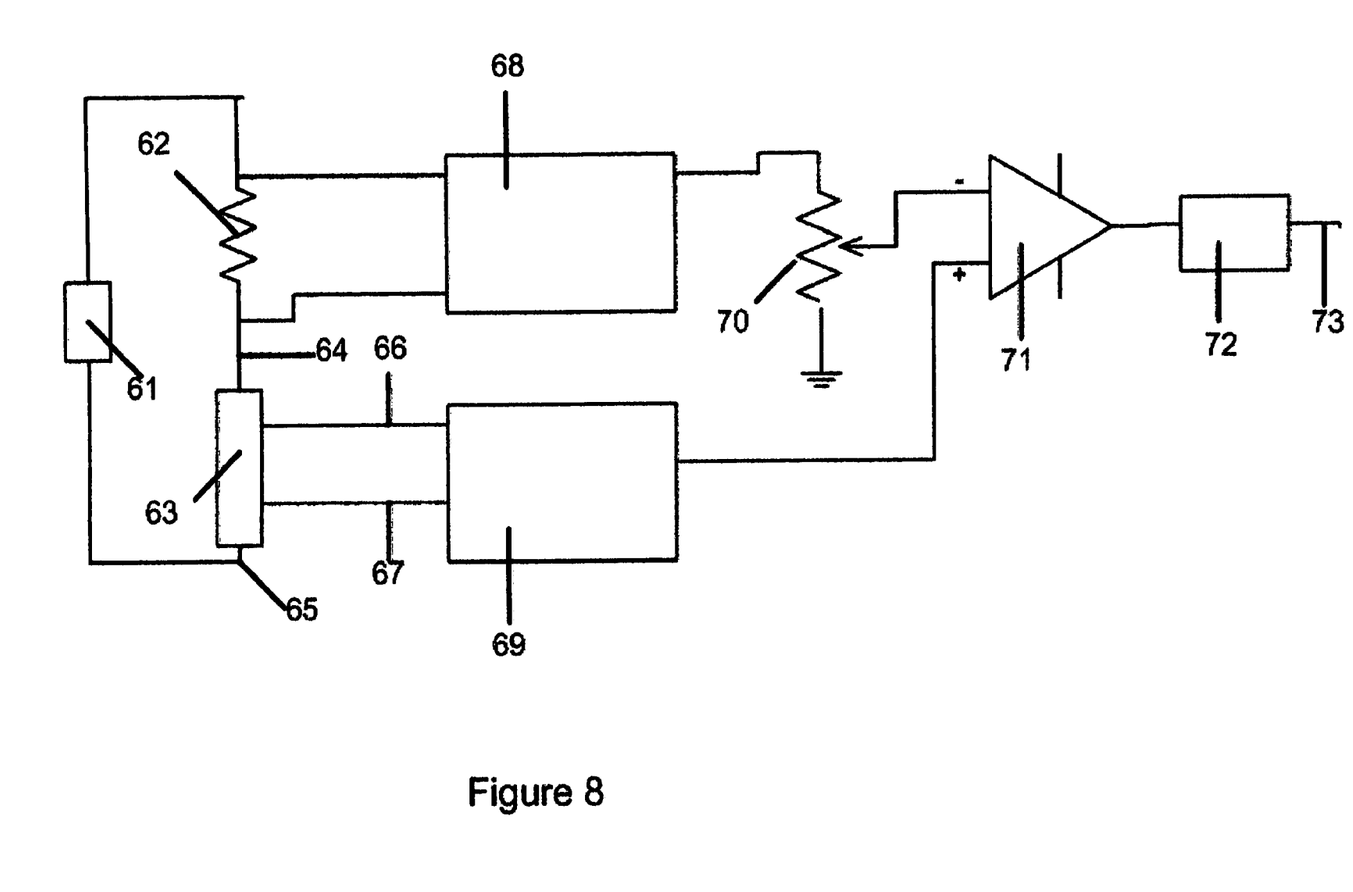
FIG. 8 is the block diagram for the data acquisition system of both embodiments.

FIG. 6 shows the block diagram of the Computing System 29 in FIG. 1, and is useful for the first embodiment. The current and signal electrodes of left hand side and right hand side assemblies, 28 and 28', respectively, are connected to this computing unit 29. Data Acquisition units 51 and 52 apply a small (10 mA, for example) high frequency (say 100 kHz) current through the outer current electrodes and sense the voltage with the inner two electrodes. Details of the data acquisition unit are shown in FIG. 8. The output of this unit is a sequence of resistance pulses, which correspond to the propagation of blood pressure pulse through the peripheral arteries. Returning to FIG. 6, a personal computer 54 stores the raw PL and PR pulses and uses DSP algorithms 55 to obtain an average peak to peak amplitude, as averaged over short intervals, say 5 to 15 minutes. The DSP algorithm is presented in FIG. 9. The averaging procedure is illustrated in FIG. 10. A Glucose monitor 53 is used for initial calibration. The subject's glucose is measured a few times (5 or so) and correlated with PL and PR peak-to-peak values, with a calibration algorithm 57. The algorithm is presented in FIG. 11. The recorded PL and PR values subsequently are compared to their values when glucose is normal to determine instances of high and low glucose. This is represented with block 56 and described in the flow chart of FIG. 12. The estimated glucose value and alerts, if any, are displayed on the display 58.

Figure 7:
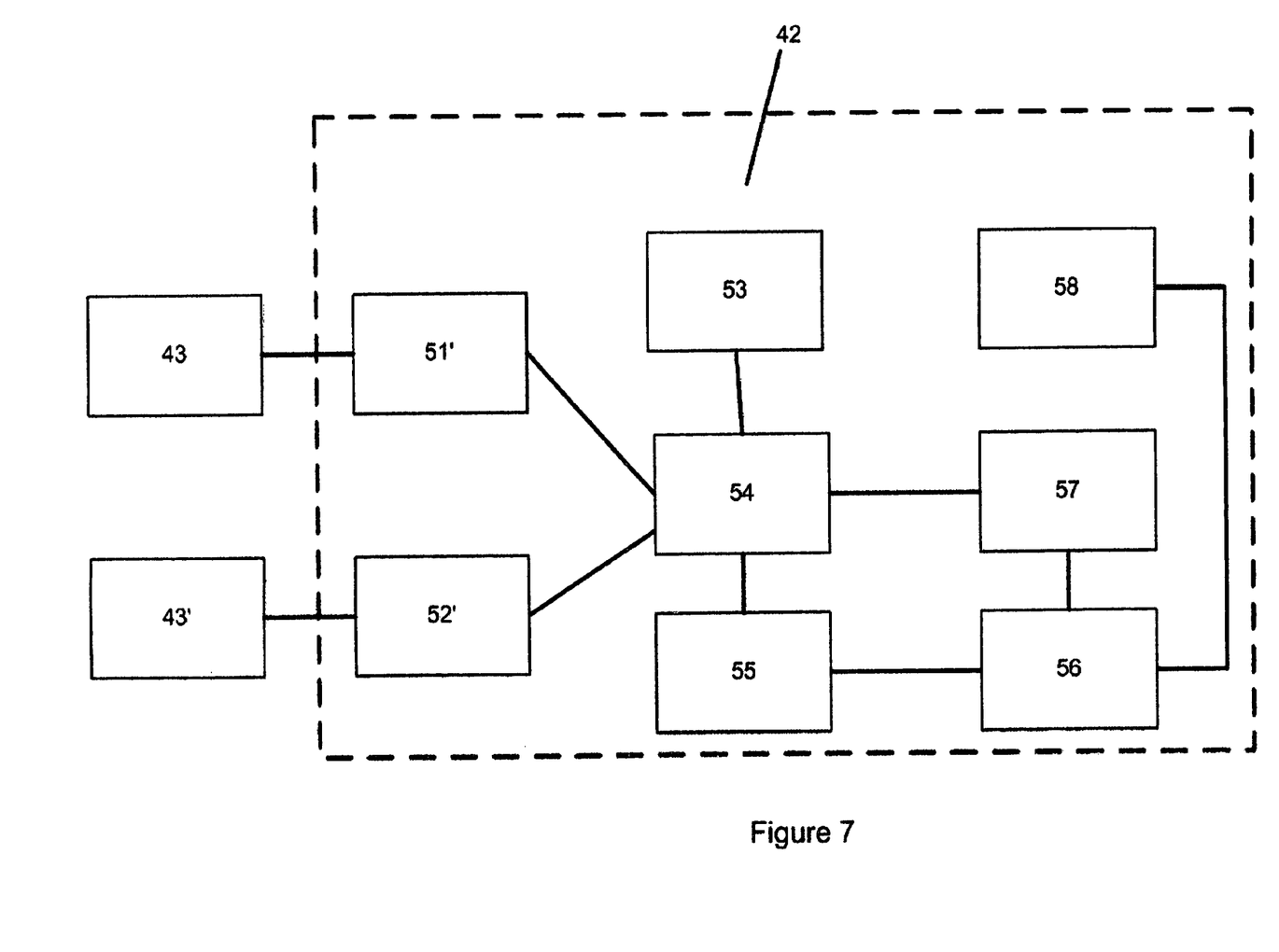
FIG. 7 is the block diagram of the computing system for the second embodiment.

FIG. 7 shows the block diagram of the Computing System 42 in FIG. 3, and is useful for both second and third embodiments. The current and signal electrodes of left hand side and right hand side assemblies, 43 and 43', are connected to this computing unit 42. Note that in the third embodiment, both the assemblies are integrated into one, as discussed above. Data Acquisition units 51' and 52' apply small (10 mA, for example) high frequency (say 100 kHz to 150 kHz) currents through the outer current electrodes and sense the voltage with the inner two electrodes. Details of the data acquisition unit are shown in FIG. 8. Note that because of the electrical insulating property of the flaccid inner wall 37, two different carrier frequencies, of say, 100 kHz and 125 kHz, may be used. The amplitude modulated signals are, however, demodulated with phase sensitive demodulators (see FIG. 8)—so, it is possible to use the same carrier frequency for both sets of current electrodes. But they could be different. It is to be noted that remainder of the blocks serve the same purposes as the blocks in FIG. 6, and are not discussed here again. The only difference is that the saline volume pulse PL' and the resistance pulse (sum of the blood volume pulse and the resistivity pulse) PR' are carried forward to the computer system where the two signals of interest (blood volume pulse and resistivity pulse) are computationally separated, by merely adding the two signals (since PL' is the inverse of the blood volume signal).

FIG. 8 shows the block diagram for designing an impedance plethysmograph. Constant current source (typically 10 mA peak to peak at 100 kHz carrier frequency) is applied to a reference resistor (typically around 100 ohms) 62 in series with the body segment 63 from which measurements are to be made. Leads 64 and 65 connect to the current electrodes referenced above. Leads 66 and 67 connect to the signal electrodes in the middle of the 4 electrode set. Both the reference signal from across the resistor 62 and the limb/digit signal from 63 are fed to a phase sensitive modulator each (68 and 69), which is supplied with the in-phase component of the carrier frequency. The outputs have a dc voltage proportional to the static resistance value of the segment. Thus, for resistor 62, the output of 68 will be proportional to the resistance value of 62. Similarly for 69, the output will be proportional to the limb/digit tissue resistance between the signal leads 66 and 67. The resistance pulse recorded is typically 0.1% to 1% of this tissue resistance, and thus quite small to directly amplify when this static resistance component is present. Thus, variable resistor 70 is used to null as much of this tissue resistance as possible. An adjustable voltage derived from the reference channel (output of 68) is subtracted from the tissue channel (output of 69) signal by summer 71. With such bucking/nulling, one can increase the modulation index substantially, to 10% or better. This signal is then amplified with an electronic amplifier 72. The output 73 is PL/PR and is a pulsatile waveform similar to that in FIG. 10.

Figure 9:
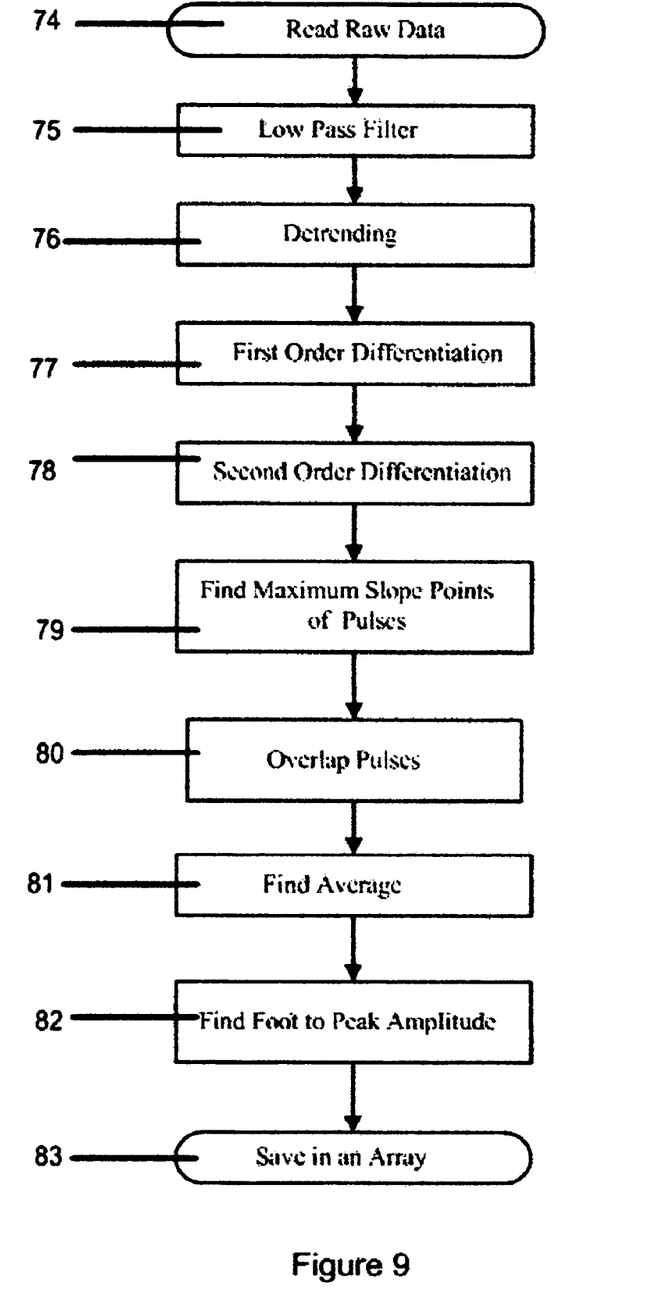
FIG. 9 is the flow chart for the digital signal processing of both embodiments.
Figure 10:
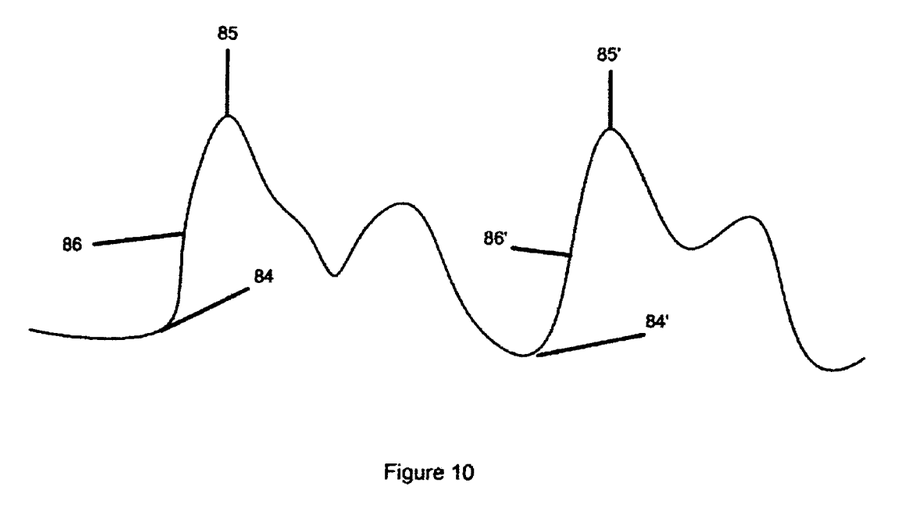
FIG. 10 is a depiction of two typical pulsatile signals recorded.

FIG. 9 presents the digital signal processing algorithm used for processing this raw pulsatile signal. Digitized signals are fed to a DSP algorithm that has the following steps: the process is started by reading in the raw digitized data in 74. The data are subject to a digital low pass filter 75 to remove power ac noise (60 Hz) and much of the effect of any motion artifacts. The data are then detrended (76) to remove slow dc drift that is typically seen in biomedical signals. A high pass filter with a cutoff frequency of 0.1 Hz or so is used. This is followed by a step of differentiation 77. Positive Zero Crossings (PZC) and Negative Zero Crossings (NZC) are identified as points of zero first slope (first order differentiation) and a second slope (second order differentiation) that is either positive or negative, respectively, in step 78. These in turn correspond to foot point and peak point of the pulse. Referring to FIG. 10, time instances 84 and 84' are the foot points and represent PZCs, while 85 and 85' are the peak points and represent NZCs. The maximum slope points (MSPs) are obtained next in step 79 by seeking points of zero second slope or points of inflection (from concave to convex) between a pair of closely spaced (say within a 200 ms or less time interval) PZC and NZC. FIG. 10 shows MSPs 86 AND 86' that occur between PZC, and NZC pairs of 84 & 85, and 84' & 85', respectively. Once the time instances of MSPs have been determined, in step 80, these pulses are overlapped with the MSPs as the reference points, and averaged (in step 81). The result is a time averaged pulse. In step 82, the foot to peak amplitude of this pulsatile signal is obtained, which is saved in an array in step 83. Thus, at the output of the digital signal processing stage, the raw pulsatile data is reduced to a foot to peak amplitude value of the averaged signal, perhaps averaged over every 10 minutes or more.

Figure 11:
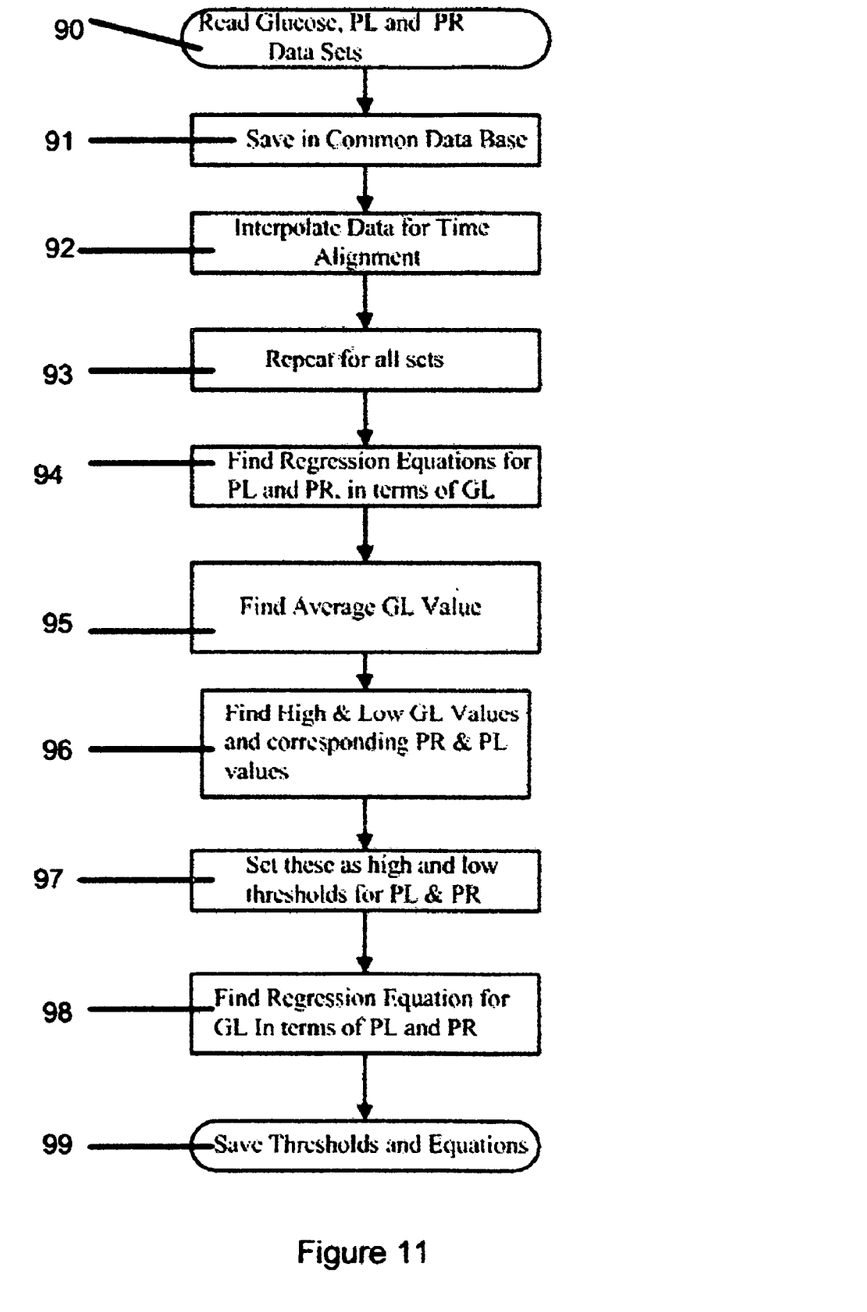
FIG. 11 is the flow chart for the calibration of the system.

FIG. 11 provides an algorithm for initial calibration of the system (block 57 in FIGS. 6 and 7). The process is started in step 90 by reading in arrays of acquired glucose, PL, and PR data. The glucose data GL is obtained via the glucose monitor 53 every 15 minutes for 5 to 10 initial measurements, and as needed there after. This calibration mechanism is not needed for most of the operation and use of the invention described herein. All these are saved in a common data base in step 91.

Data interpolation in step 92 may be needed to ensure that the three sets of data correspond to a close time instant. In step 93, repeat this for all the 5 to 10 sets of data. In step 94, find best fit regression equations for PL and PR in terms of glucose level GL and a constant. Thus, these equations may be of a linear form given by PL=a×GL+b; and PR=c×GL+d, where PL, GL, and PR are the set of 5 to 10 stored values, a and c are the weighing coefficients for GL, and b and d are constants. In step 95, find the average GL value. In step 96, find the high and low GL values that are 1 SD (standard deviation) away from this average GL value. Also, find the corresponding PR and PL values for these high and low GL values. In step 97, set high and low threshold values for PL and PR as these computed values. In step 98, develop a regression equation for estimating GL value in terms of PL and PR values. This regression equation may, for example be linear, and allow one to express GL as e×PL+f×PR+g, where e and f are weighing coefficients and g is a constant, as obtained from a regression equation. All these thresholds and equations are saved in step 99, for easy accessibility.

Figure 12:
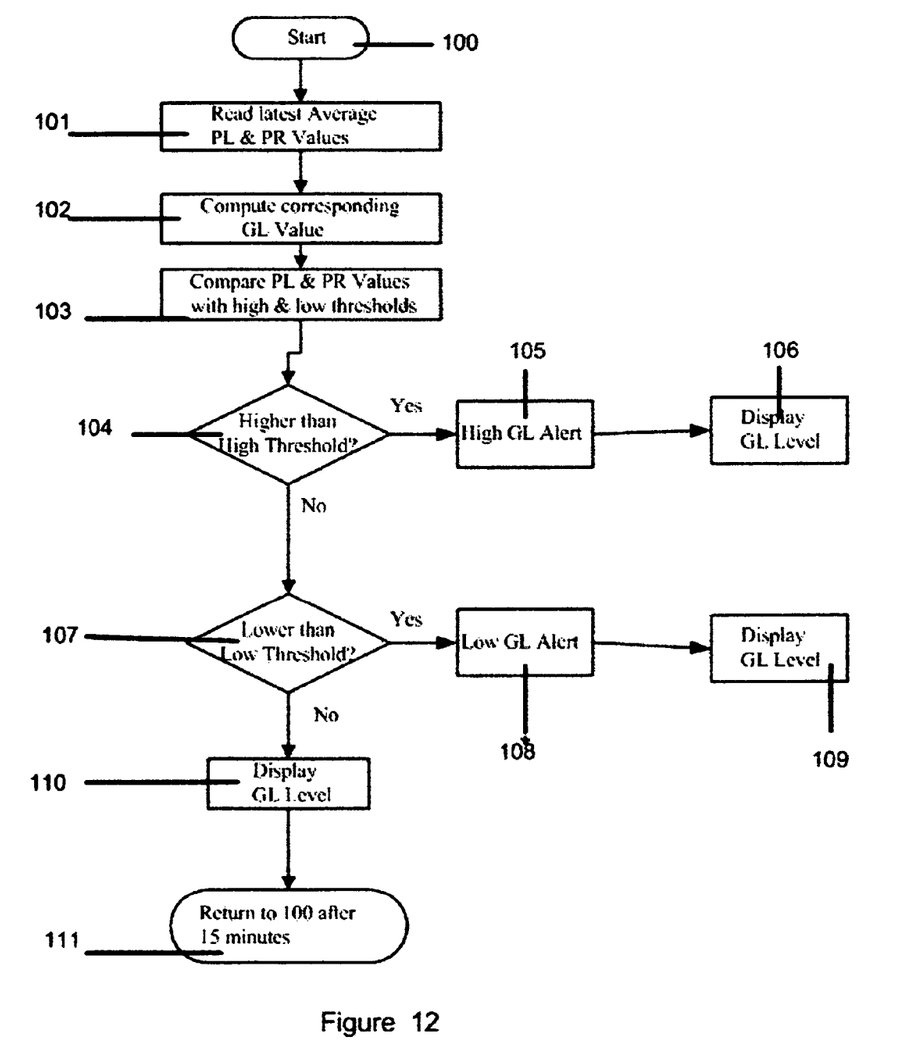
FIG. 12 is the flow chart for estimation of glucose and provision of high and low glucose alerts.

FIG. 12 corresponds to the block 56 in FIGS. 6 and 7 and is concerned with glucose monitoring and display, on Display 58, of an averaged glucose value and alerts of high or low glucose, if any. The algorithm starts in 100. In step 101, the latest averaged PL and PR values are read into an array. In step 102, the corresponding Glucose level is computed, with the aid of a previously determined regression equation (see the previous paragraph). In step 103, the PL and PR values recently acquired are compared with PL and PR high and low thresholds. In step 104, if PL and PR values are higher than their set high threshold values, a high glucose alert and the computed glucose level are displayed in steps 105 and 106, respectively. In a similar manner, if PL and PR values are lower than their set low threshold values, step 107 will initiate the steps of 108 and 109 to display a low glucose alert along with a display of the computed glucose value. If neither situation is true, then the computed glucose level is presented on the Display 58, in step 110. In step 111, the algorithm returns to the starting step, 100, once every 15 minutes or so.

While I have shown and described the preferred embodiments of my invention, it will be understood that the invention may be embodied otherwise than as herein specifically illustrated or described, and that certain changes in form and arrangement of parts and the specific manner of practicing the invention may be made within the underlying idea or principles of the invention.

What is claimed is:

1. Apparatus for noninvasive measuring of blood glucose level comprising:
    a first digit encircling liquid chamber with a first electrode assembly affixed to an inner surface of an outer wall of the chamber, the first electrode assembly including a first pair of spaced-apart signal electrodes and a pair of electrodes positioned beside the first pair of spaced-apart signal electrodes through which an electric current is fed into the chamber;
    a second digit encircling liquid chamber with a second electrode assembly affixed to an inner surface of an outer wall of the chamber, the second electrode assembly including a second pair of spaced-apart signal electrodes and a pair of electrodes positioned beside the second pair of spaced-apart signal electrodes through which an electric current is fed into the chamber;
    liquid in the first chamber having electrical conductivity substantially equal to electrical conductivity of fluid in the digit;
    liquid in the second chamber having electrical conductivity substantially more than the electrical conductivity of fluid in the digit; and
    pulsatile signal processing circuitry connected to the first and second pairs of signal electrodes to compare electrical signals on the two pairs of signal electrodes to calibration signals received during known glucose levels to thereby distinguish between normal glucose concentration, high glucose concentration, and low glucose concentration.

2. The apparatus of claim 1 in which each chamber has an encircling rigid vertical wall, a closed bottom, and an open top through which the digit is to be inserted; and the electrode assembly is affixed to an inside surface of the vertical wall.

3. The apparatus of claim 1 in which each chamber has an annular volume defined by an encircling rigid outer wall, a flexible inner wall, and two flexible end members sealingly joining the inner and outer walls;
    the electrode assembly is affixed to an inside surface of the outer wall; and
    an electrode assembly is additionally affixed to the outer surface of the flexible inner wall of at least one chamber to contact the surface of the digit.

4. The apparatus of claim 1 in which the signal processing circuitry comprises:
    real time signal acquisition, processing, and storing;
    a process for removing motion artifacts and noise due to instrumentation and ac power;
    storage of signals acquired during calibration at known blood glucose levels;
    comparison of trends in stored signals with calibration signals; and
    signature analysis.

5. A method for measuring blood glucose level comprising:
    encircling a first digit with a first digit encircling liquid chamber with a first electrode assembly including a first pair of spaced-apart signal electrodes and a pair of electrodes positioned beside the first pair of spaced-apart signal electrodes through which an electric current is fed into the chamber;
    encircling a second digit with a second digit encircling liquid chamber with a second electrode assembly including a second pair of spaced-apart signal electrodes and a pair of electrodes positioned beside the second pair of spaced-apart signal electrodes through which an electric current is fed into the chamber;
    providing a liquid in the first chamber having electrical conductivity substantially equal to the electrical conductivity of the fluid in the digit;
    providing a liquid in the second chamber having electrical conductivity substantially more than the electrical conductivity of the fluid in the digit; and
    using a pulsatile signal processing circuitry connected to the first and second pairs of signal electrodes to compare electrical signals on the two pairs of signal electrodes to calibration signals received during known glucose levels to thereby distinguish between normal glucose concentration, high glucose concentration, and low glucose concentration.

6. Apparatus for noninvasive measuring of blood glucose level comprising:
    a digit encircling liquid chamber having an annular volume defined by an encircling rigid outer wall, a flexible inner wall, and two flexible end members sealingly joining the inner and outer walls;
    a first electrode assembly affixed to an inner surface of the outer wall, the first electrode assembly including a first pair of spaced-apart signal electrodes and a pair of electrodes positioned beside the first pair of spaced-apart signal electrodes through which an electric current is fed into the chamber;

a second electrode assembly affixed to an outer surface of the inner wall to contact the digit, the second electrode assembly including a second pair of spaced-apart signal electrodes and a second pair of electrodes positioned beside the second pair of spaced-apart signal electrodes through which an electric current is fed;

liquid in the chamber having electrical conductivity;

pulsatile signal processing circuitry connected to the first and second pairs of signal electrodes to compare electrical signals on the two pairs of signal electrodes to calibration signals received during known glucose levels to thereby distinguish between normal glucose concentration, high glucose concentration, and low glucose concentration.

* * * * *